US012185971B2

(12) United States Patent
Poulter

(10) Patent No.: US 12,185,971 B2
(45) Date of Patent: Jan. 7, 2025

(54) KNIFE FOR CANNULATED SURGERY

(71) Applicant: Warsaw Orthopedic, Inc., Warsaw, IN (US)

(72) Inventor: Gregory Poulter, Zionsville, IN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 334 days.

(21) Appl. No.: 16/906,734

(22) Filed: Jun. 19, 2020

(65) Prior Publication Data

US 2020/0397460 A1 Dec. 24, 2020

Related U.S. Application Data

(60) Provisional application No. 62/864,176, filed on Jun. 20, 2019.

(51) Int. Cl.
*A61B 17/3211* (2006.01)
*A61B 17/34* (2006.01)

(52) U.S. Cl.
CPC ...... *A61B 17/3211* (2013.01); *A61B 17/3421* (2013.01)

(58) Field of Classification Search
CPC ............ A61B 17/3211; A61B 17/3421; A61B 17/3209
See application file for complete search history.

(56) References Cited

U.S. PATENT DOCUMENTS

| | | | |
|---|---|---|---|
| 2009/0204126 A1* | 8/2009 | Le | A61B 17/0467 606/138 |
| 2012/0277761 A1* | 11/2012 | Boling | A61B 17/3468 606/129 |
| 2013/0053875 A1* | 2/2013 | Scheller | A61F 9/0133 606/170 |
| 2013/0066164 A1* | 3/2013 | Nakamura | A61B 17/22031 606/1 |
| 2018/0125520 A1* | 5/2018 | Lehn, Jr. | B26B 1/08 |

* cited by examiner

*Primary Examiner* — Anh T Dang
(74) *Attorney, Agent, or Firm* — Sorell, Lenna & Schmidt, LLP

(57) ABSTRACT

A surgical knife for introduction through a cannula includes a handle portion with an angled transition to a reduced portion. A blade connected to the reduced portion has a width perpendicular to the longitudinal axis that is equal to or greater than half the effective handle dimension. The blade is connected to the handle so that the outer transverse edge of the blade is outwardly offset from the outer surface of the handle. The blade width is preferably 80% of the effective dimension of the handle. The blade includes a cutting edge that extends across the width of the blade. In use, the knife can be extended through a cannula to make a first incision, retracted and rotated 180°, and then make another incision colinear with the first incision to create a single incision having a length greater than the width of the cannula.

20 Claims, 4 Drawing Sheets

KNIFE FOR CANNULATED SURGERY

PRIORITY CLAIM

This application is a utility filing from and claims priority to U.S. Provisional No. 62/864,176, filed on Jun. 20, 2019, the entire disclosure of which is incorporated herein by reference.

BACKGROUND

Spinal surgery has advanced considerably over the last half-century from fully open surgeries to minimally invasive surgeries. The addition of robotic guidance for surgery has allowed for precise placement of instruments in the spine, often through cylindrical cannulae of a fixed diameter placing a knife through a cannula allows for very precise and safe placement of incisions. However, the physical constraints of placing a scalpel blade through a tubular cannula creates an incision that is not large enough to accommodate round instruments placed through the same cannula. In the ideal case, the maximum size of a scalpel that can be placed through a cannula of inner diameter D is of equal length D. The incision that this scalpel can make will have edges on either side of the blade totaling a circumferential length of 2×D. The circumferential length of edges needed to accommodate a round instrument passed through the same cannula or trocar is πD or 3.14×D. Thus, the ideal length of an incision to accommodate a round instrument of diameter D is 1.57×D.

Current knife handles that are designed to work through cannulae common with robotic and other minimally invasive systems do not take into account the need for a larger incision which results in excessive stretching and damage to the soft tissues as the additional cannula or instrument is introduced. On the other hand, larger scalpels that are employed outside of a working cannula do not allow for the necessary precision in sizing and placement of incisions.

There is a need for a knife and knife handle that can be placed through a constrained cannula with the ability to create an ideal incision to allow the use of instrumentation also designed to work through a cannula of the same diameter.

SUMMARY OF THE DISCLOSURE

A surgical knife for percutaneous introduction through a cannula comprises an elongated handle portion defining a longitudinal axis and having an outer surface defining an effective handle dimension perpendicular to the longitudinal axis that is sized for the handle portion to pass through the cannula in the direction of the longitudinal axis. The knife includes a reduced portion connected to the handle portion by a transition portion, the reduced portion having an effective dimension perpendicular to the longitudinal axis that is equal to or greater than half the effective handle dimension but less than the effective handle dimension. A blade is connected to a distal end of the reduced portion. The blade is connected to the handle so that said outer transverse edge of the blade is offset from the outer surface of the handle perpendicular to the longitudinal axis and outside the outer surface in relation to the longitudinal axis.

The blade has a width perpendicular to the longitudinal axis that is equal to or greater than one-half the effective handle dimension but less than the effective handle dimension. Preferably, the blade width is 80% of the effective dimension of the handle. The blade includes a cutting edge that extends across the width of the blade, so that the cutting edge spans a width that is 80% of the effective dimension of the handle.

When the knife is extended through the cannula, the blade shifts laterally relative to the cannula upon exiting the distal end of the cannula. The cutting edge can form an incision that is longer than the radius of the cannula. After making an initial incision, the knife can be retracted, rotated 180° and a second incision can be made at the opposite side of the cannula that is colinear with the first incision to form a single incision with a length greater than the diameter of the catheter.

DETAILED DESCRIPTION

Figure 1:
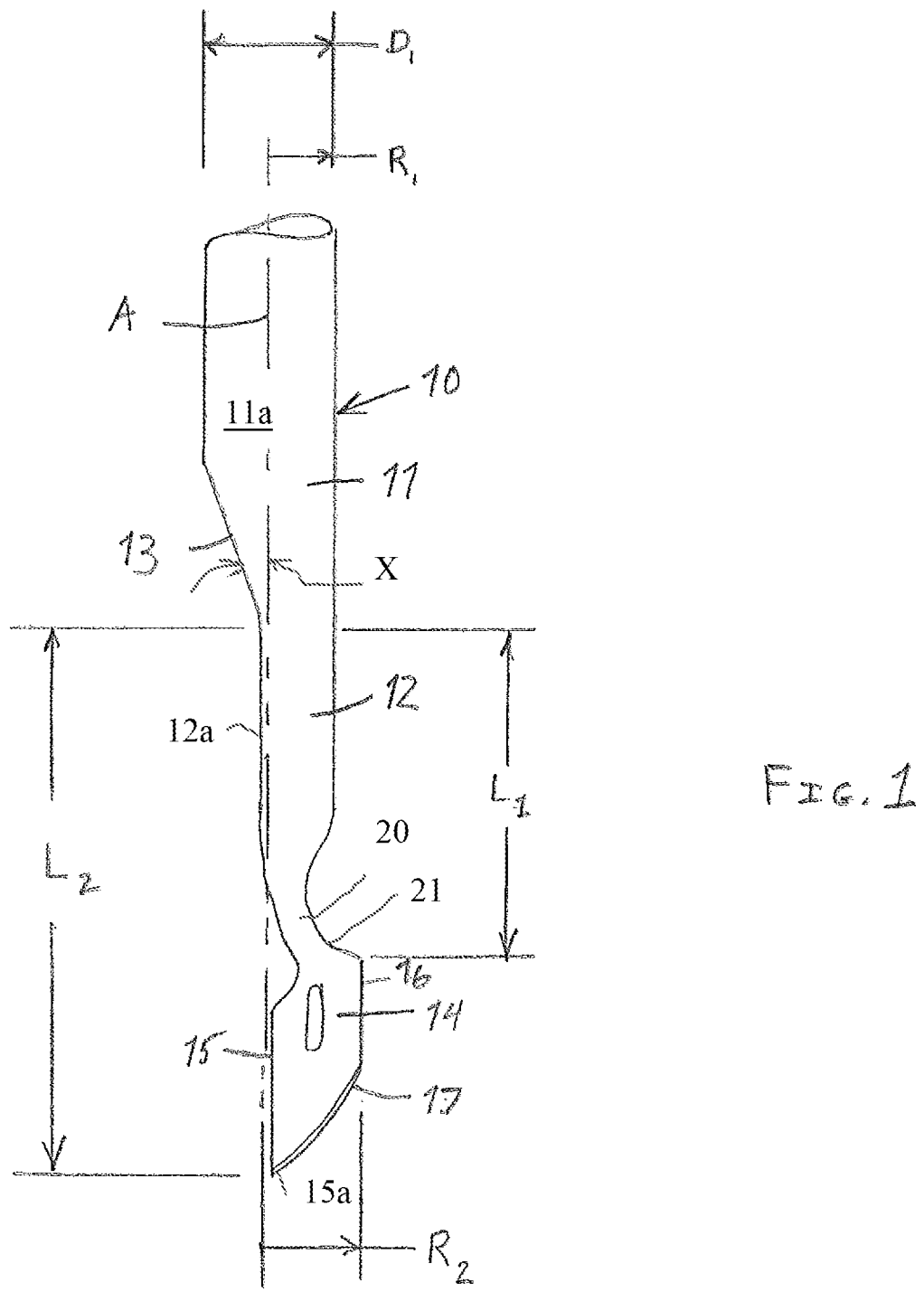
FIG. 1 is a side view of a knife for cannulated surgery according to one embodiment of the present disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles disclosed herein as would normally occur to one skilled in the art to which this disclosure pertains.

In accordance with the present disclosure, a knife 10 is provided, as shown in FIG. 1, which is capable of being introduced through a conventional cannula but still capable of producing an incision that is larger than the cannula diameter. The knife 10 includes a handle 11 that is configured to slidingly engage the inner surface of a cannula, such as cannula C shown in FIG. 2, in the manner shown in FIG. 4. The proximal end of the handle can be configured for manual engagement by the surgeon or to integrate into an automated surgical apparatus. The handle 11 can have a cross-sectional shape that conforms to the cross-sectional shape of the bore B defined by the cannula C, which would typically be cylindrical. The handle 11 has an outer surface 11a that defines a dimension D1 perpendicular to the longitudinal axis A of the handle that is nearly equal to the effective internal dimension D1+ of the cannula C to allow the knife, and ultimately the knife blade 14, to be precisely placed in a trajectory that is determined by the cannula. It is understood that "effective dimension" in the context of the present application is the dimension in the plane of the blade 14 (see below), and that the dimensions of the handle and the cannula are typically a diameter since the two components are typically cylindrical.

The handle 11 includes a transition portion 13 at the distal end of the handle 11 that transitions the cross-sectional configuration of the handle to a reduced portion 12 having a reduced effective dimension in relation to the proximal extent of the handle 11. The transition portion 13 provides a surface that is angled relative to the longitudinal axis A and extends from the outer surface of the handle portion to the axis, as shown in FIG. 1. It is contemplated that the surface of the transition portion 13 corresponds to the cross-sectional configuration of the cannula C—i.e., for a cylindrical cannula the surface of the transition portion 13 is also circular. It is understood, however, that for the purposes of the transition portion 13 described herein, the transition portion can be in the form of an angled rib.

Figure 3:
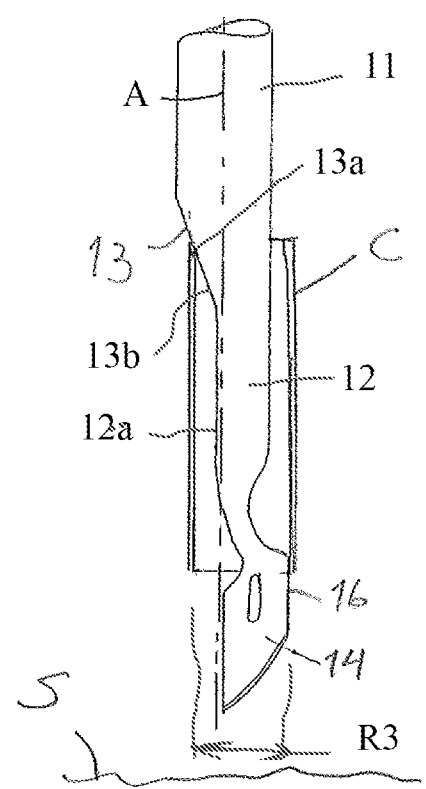
FIG. 3 is side partial cut-away view of the knife and cannula shown in FIG. 2 with the knife advanced beyond the end of the cannula.

In one embodiment, the reduced effective dimension of the reduced portion is equal to or greater than one-half the dimension D1, or equal to or slightly greater than the radius R1 of the handle, as depicted in FIG. 1. In one specific embodiment, the term "slightly" means no more than a 10% variation from the referenced dimension. The reduced portion 12 extends a length L1 that is equal to or less than a length L of cannula C through which the knife is introduced to access the skin S at a surgical site, as shown in FIG. 3. The cross-section of the portion 12 is configured to conform to the cross-section of the cannula bore B. In one embodiment, the portion 12 follows the same cross-section as the handle 11, but has a truncated surface 12a at one side of the cross-section, as shown in FIG. 1. Thus, for a cylindrical handle having a circular cross-section, the portion 12 has a cross-section of a segment of that circular cross-section formed by a chord (corresponding to the surface 12a) extending across the cross-section slightly offset from the midline or axis A of the circular cross-section of the handle. Alternatively, the truncated surface 12a can generally conform to the cross-section of the cannula i.e., circular, albeit at a smaller radius than the cannula. In this alternative embodiment, the entire reduced portion 12 can have a circular cross-section. A similar approach can be taken for non-circular cross-sections of the cannula, handle and reduced portion.

Figure 2:
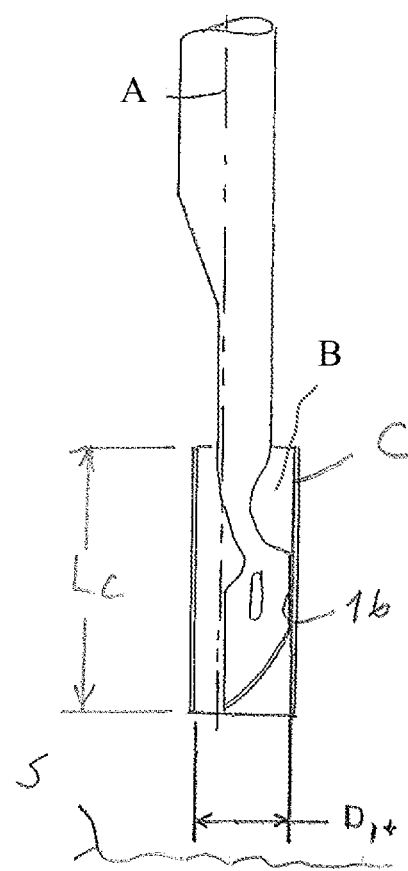
FIG. 2 is side partial cut-away view of the knife of FIG. 1 disposed within a cannula.

A planar blade portion 14 is attached to or integral with the end of the reduced portion 12, connected by a bridge segment 20 of the reduced portion, discussed in more detail herein. The blade 14 has an inner edge 15 that extends generally parallel to the longitudinal axis A of the handle 11, and an opposite outer edge 16 that also extends generally parallel to the axis A. As shown in FIGS. 2-3, the outer edge 16 bears against the inner surface, or bore B, of the cannula C as the knife is advanced along the cannula. The blade has a width R2 in the plane of the blade between the inner and outer edges 15, 16 that is greater than the radius R1 of the handle. However, the blade 14 is offset relative to the handle so that the outer edge 16 is radially offset from the outer surface of the handle 11, as depicted in FIG. 1. In the illustrated embodiment, the blade is offset so that the tip 15a is on or nearly on the midline or axis A of the knife. In one specific embodiment, the width R2 is about 1.3 times the radius R1 of the handle, and thus nearly 1.3 times the radius of the cannula C. However, the width R2 of the blade 14 is less than the inner dimension D1+ of the cannula C so that the blade can be readily advanced through the cannula, as depicted in FIGS. 2-3.

As shown in FIG. 1, the truncated surface 12a coincides with the inner edge 15 of the blade. If the blade width R2 is nearly equal to the inner diameter D1+ of the cannula, the outer edge 16 of the blade and the truncated surface 12a of the reduced portion 12 will contact the bore B to initially guide the knife through the cannula until the transition portion 13 reaches the proximal end of the cannula. However, it is contemplated that the truncated surface 12a can be offset from the inner edge 15 of the blade. For instance, in the embodiment shown in FIG. 3, the truncated surface 12a can be aligned with the contact point 13a (discussed below), in which case the transition portion is shortened, commencing at the contact point 13a and extending to the outer surface of the handle 11.

As shown in FIG. 1, the blade 14 has a sharpened cutting edge 17 at the distal end of the blade. The cutting edge is configured to create an incision in tissue as the blade is advanced into the skin S. The cutting edge terminates at a length L2 from the end of the transition portion 13 of the knife. The length L2 is greater than the length Lc of the cannula.

In using the knife 10, the surgeon uses the handle 11 to pass the blade 14 and reduced portion 12 into the cannula C, as shown in FIG. 2. In this first step, the outer edge 16 of the blade 14 can contact the bore B of the cannula to guide the knife into the cannula. As the knife is advanced further into the cannula, the angled transition portion 13 contacts the inner wall of the cannula, which gradually shifts the outer edge 16 of the blade to the inner surface of the cannula, as shown in FIG. 3. The length L1 between the proximal end of the knife and the beginning of the angled transition portion 13 is calibrated so that the transition portion 13 contacts the cannula C before the outer edge 16 contacts the cannula. As the knife is advanced further through the cannula, the transition portion 13 gradually forces the blade edge 16 toward contact with the cannula bore. In one specific embodiment, the length and angle of the transition portion 13 and the length L1 are calibrated in relation to the length Lc of the cannula so that the blade edge 16 just exits the distal end of the cannula C when the point 13a on the transition portion contacts the proximal end of the cannula. In other words, the dimension R3 between the outer edge 16 of the blade and the contact point 13a of the transition portion equals the inner diameter D1+ of the cannula. The contact point 13a thus corresponds to the point at which the blade of the knife has exited the distal end of the cannula.

Alternatively, the dimension R3 can be slightly less than the cannula inner diameter D1+ so that the outer edge 16 contacts the cannula before the contact point 13a reaches the proximal end of the cannula. In this embodiment, the bridge segment 20 can be configured to provide some flexibility to the interface between the blade 14 and the handle 11 so that the blade can flex as the contact between the transition portion 13 and the cannula bore B tries to force the blade edge 16 against the bore. However, when the knife has advanced far enough into the cannula, i.e., to point 13a, the blade 14 clears the distal end of the cannula and a relief recess 21, defined by the bridge segment 20, passes by the distal end of the cannula.

Figure 4:
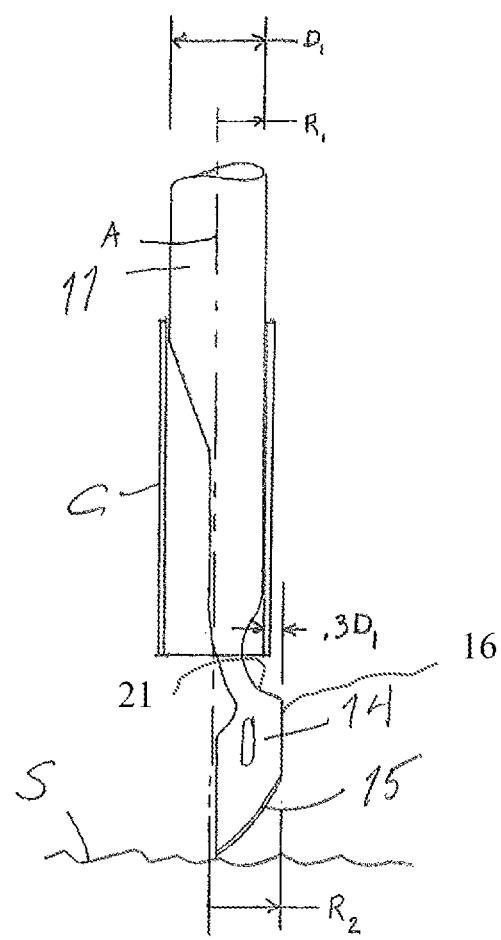
FIG. 4 is side partial cut-away view of the knife and cannula shown in FIG. 3 with the knife advanced further beyond the end of the cannula into contact with the patient's skin prior to making an incision.

As the knife is advanced farther, the transition portion 13 gradually forces the handle 11 closer to the opposite surface of the bore until the handle 11 is fully concentrically disposed within the cannula, as shown in FIG. 4. The relief recess 21 provides clearance for the bridge segment 20 to exit the cannula. In this position, the blade 14 is clear of the distal end of the cannula. The handle thus becomes constrained to follow the path of the cannula so that longitudinal movement of the knife handle constrains the blade accordingly. As the knife is advanced further through the cannula, the cutting edge 15 of the blade makes an incision in the skin S. It can be appreciated from FIG. 4 that the cutting edge 15 extends outside the outer diameter of the cannula C. Since the blade 14 has a width R2 that is greater than the radius R of the handle 11, the cutting edge 15 will make an incision that extends from the midline or axis A outside the outer diameter of the cannula. The knife is then retracted within the cannula so that the blade 14 is retracted from the tissue.

With the blade clear of the tissue, the handle 11 can be rotated 180° so that the blade is the mirror image of FIG. 4 with the cutting edge 15 extending to the left side, rather than to the right. The knife handle is then advanced again through the cannula C so that the blade creates a second incision diametrically opposite the first incision. Alternatively, the knife can be rotated in 90° increments to create two perpendicular incisions or at any particular angular increments to make an incision in the skin S.

Prior cutting blades are limited to the inner diameter of the cannula with the blade extending across the inner diameter of the cannula. In the illustrated embodiment, two passes of the blade 14 combine to make a single incision that it 1.6 times the dimension D1 of the handle 11, which is almost 1.6 times the inner dimension D1+ of the cannula C. The reduced portion 12 of the knife 10 of the present disclosure allows the cutting blade 14 to have a width that is greater than the radius R1 and diameter of the cannula C, which results in an incision having a length greater than the diameter of the cannula.

The cutting blade 14 can have a width R2 between the edges 15, 16 that is much greater than the dimension R1 of the handle and much greater than one-half the inner diameter D1+ of the cannula, and even nearly equal to the inner diameter D1+. With a larger width R2, the cutting blade can still be advanced through the cannula. However, in order for the cutting edge 17 to extend beyond the outer diameter of the cannula, as depicted in FIG. 4, the contact point 13a of the transition portion is closer to the reduced portion 12, such as point 13b. At that point, the blade has exited the cannula, and as the handle is moved further through the cannula the angled transition portion 13 moves the blade laterally with the clearance provided by the relief recess 21. Such a configuration would produce an incision having a length of almost twice the dimensions D1 or D1+, but such an incision width is unnecessary for an instrument that is advanced through the same cannula C having the same inner diameter D1+. Of course, the larger incision can be used for instruments advanced through a different, larger, cannula.

It has been found that the ratio of 1.57×D1, rounded up to 1.6×D1 provides an optimum length incision to accept an instrument guided through the cannula C. A shorter incision length is too small to accept the additional instrument which can require unnecessary force to introduce and lead to unnecessary trauma to the skin or tearing at the incision. A larger incision is unnecessary since the instrument guided through the same cannula cannot be any larger than the cannula bore B. With this ratio, a blade width R2 of 0.8×D1, or 80% of the effective dimension D1 of the handle, produces an optimum incision. This blade width leads to the outer edge 16 of the blade 14 extending beyond the outer surface of the cannula C by a dimension of 0.3×D1, as illustrated in FIG. 4.

It is contemplated that the proximal end of the handle (not shown) can include a bayonet fitting to be placed through a closed trocar and still permit the handle 11 to engage a separate guiding effector or cannula.

It can be appreciated that the dimensions of the knife 10 are dictated in a large degree by the dimensions of the cannula. The cannula has an inner diameter of the bore B of D1+ and the diameter of effective dimension D1 of the handle 11 of the knife is necessarily slightly less than the cannula diameter D1+ with the goal being to provide a close running clearance between the handle and the cannula to accurately guide the cutting edge of the blade. The length of the reduced portion 12 is less than or equal to the length Lc of the cannula so that the blade clears the end of the cannula just as the transition portion contacts the proximal end of the cannula. The width R2 of the blade is less than the effective dimension D1 of the handle, but greater than one-half the dimension D1. As expressed above, the blade width R2 is optimally 0.8*D1. The transition portion 13 is angled relative to the longitudinal axis at an angle that shifts the blade 14 laterally relative to the cannula, once it exits the cannula, as quickly as possible before the cutting edge 17 contacts the skin S (FIG. 4). Thus, in one specific embodiment, the transition portion 13 is arranged at an angle X that is at least 45, and preferably 60-70°.

As indicated above, the blade can have a width R2 nearly equal to the inner diameter D1+ of the cannula, as well as the optimum width of 80% of the dimension D1 of the handle. In accordance with the present disclosure, the blade can have any width between the maximum and optimum widths. The length and/or angle of the transition portion 13 can be adjusted accordingly so that the contact point 13a, 13b coincides with the exit of the blade from the cannula, or nearly coincides with the exit where the bridge segment 20 flexes as described above.

It is contemplated that the entire surgical knife 10 is formed as one piece. However, one or more components of the knife can be separate but connected or attached to each other. For instance, the handle 11 can be separate from the blade 14 or separate from the bridge segment 20 that carries the blade 14. Alternatively, the reduced portion 12 can be separate from the transition portion 13 of the handle 11, or the transition portion 13 can be separate from the proximal part of the handle 11. The separate components of the knife can be connected or attached in a permanent or removable manner, as is known in the art.

The present disclosure should be considered as illustrative and not restrictive in character. It is understood that only certain embodiments have been presented and that all changes, modifications and further applications that come within the spirit of the disclosure are desired to be protected.

What is claimed is:

1. A surgical knife for introduction through a cannula defining a bore having an effective cannula diameter, the knife comprising:

an elongated handle portion defining a longitudinal axis and having an outer surface defining an effective handle dimension perpendicular to said longitudinal axis that is sized for the handle portion to pass through the cannula in the direction of said longitudinal axis; and a blade having a proximal end connected said handle, said blade having opposite transverse inner and outer edges each extending parallel to said longitudinal axis, said inner and outer edges defining a width therebetween perpendicular to said longitudinal axis that is equal to or greater than one-half the effective handle dimension and less than the effective handle dimension, said blade including a cutting edge at a distal end of said blade extending continuously from said inner edge to said outer edge, said cutting blade having a distal end that extends from said inner edge and an opposite proximal end that extends from said outer edge such that said proximal end is positioned proximal to said distal end along said longitudinal axis, said cutting edge extending across said width and configured to create an incision in skin, wherein said blade is connected to said handle so that said longitudinal axis does not intersect said cutting edge and is offset from said inner and outer edges, wherein said outer edge of said blade is offset from said outer surface of said handle perpendicular to said longitudinal axis and outside said outer surface in relation to said longitudinal axis.

2. The surgical knife of claim 1, wherein said width of said blade is no greater than eighty percent (80%) of the effective handle dimension.

3. The surgical knife of claim 1, wherein:
said handle portion includes a reduced portion having an effective dimension perpendicular to said longitudinal axis that is equal to or greater than half the effective handle dimension but less than the effective handle dimension; and
said proximal end of said blade is connected to a distal end of said reduced portion.

4. The surgical knife of claim 3, further comprising a transition portion connecting a distal end of said handle portion to a proximal end of said reduced portion, the transition portion defining an angled surface that contacts the bore of the cannula as the handle is advanced through the cannula.

5. The surgical knife of claim 4, wherein said angled surface is defined at an angle of 45-70 degrees relative to said longitudinal axis.

6. The surgical knife of claim 4, wherein said blade is connected to said reduced portion by a bridge segment, said bridge segment defining a relief recess adjacent said outer transverse edge of said blade.

7. The surgical knife of claim 4, further comprising the cannula, wherein the cannula has a cannula length, and wherein said reduced portion has a length parallel to said longitudinal axis between said handle and said blade that is less than the cannula length.

8. The surgical knife of claim 4, wherein said handle portion, said reduced portion, said transition portion and said blade are integrally formed.

9. The surgical knife of claim 1, wherein said knife includes an arcuate bridge between said handle and said blade, said edges each including a length from said bridge to said cutting edge, said lengths each extending parallel to said longitudinal axis.

10. The surgical knife of claim 9, wherein said bridge has a width that is less than said width of said blade.

11. The surgical knife of claim 1, wherein said inner edge extends parallel to said longitudinal axis along an entire length of said inner edge.

12. The surgical knife of claim 1, wherein said longitudinal axis is a central longitudinal axis, said inner edge being offset from said central longitudinal axis.

13. A surgical knife assembly comprising:
a cannula having an effective cannula diameter and a cannula length; and
a surgical knife including:
an elongated handle portion defining a longitudinal axis and having an outer surface defining an effective handle dimension perpendicular to said longitudinal axis that is sized for the handle portion to pass through the cannula in the direction of said longitudinal axis; and
a blade having a proximal end connected said handle, said blade having opposite transverse inner and outer edges each extending parallel to said longitudinal axis along their entire lengths such that the outer edge faces away from the inner edge, said inner and outer edges defining a width therebetween perpendicular to said longitudinal axis that is equal to or greater than one-half the effective handle dimension and less than the effective handle dimension, said blade including a cutting edge at a distal end of said blade, said cutting edge extending continuously from said inner edge to said outer edge across said width and configured to create an incision in skin, wherein said blade is connected to said handle so that said longitudinal axis does not intersect said cutting edge and is offset from said inner and outer edges, said cutting blade having a distal end that extends from said inner edge and an opposite proximal end that extends from said outer edge such that said proximal end is positioned proximal to said distal end along said longitudinal axis, wherein said outer edge of said blade is offset from said outer surface of said handle perpendicular to said longitudinal axis and outside said outer surface in relation to said longitudinal axis.

14. The surgical knife of claim 13, wherein said width of said blade is no greater than eighty percent (80%) of the effective handle dimension.

15. The surgical knife of claim 13, wherein:
said handle portion includes a reduced portion having an effective dimension perpendicular to said longitudinal axis that is equal to or greater than half the effective handle dimension but less than the effective handle dimension; and
said proximal end of said blade is connected to a distal end of said reduced portion.

16. The surgical knife of claim 15, further comprising a transition portion connecting a distal end of said handle portion to a proximal end of said reduced portion, the transition portion defining an angled surface that contacts the bore of the cannula as the handle is advanced through the cannula.

17. The surgical knife of claim 16, wherein said angled surface is defined at an angle of 45-70 degrees relative to said longitudinal axis.

18. The surgical knife of claim 16, wherein said blade is connected to said reduced portion by a bridge segment, said bridge segment defining a relief recess adjacent said outer transverse edge of said blade.

19. The surgical knife of claim 16, in which the cannula has a cannula length, and wherein said reduced portion has a length parallel to said longitudinal axis between said handle and said blade that is less than the cannula length.

20. The surgical knife of claim 16, wherein said handle portion, said reduced portion, said transition portion and said blade are integrally formed.

* * * * *